United States Patent
Wariar et al.

(10) Patent No.: US 9,592,327 B2
(45) Date of Patent: Mar. 14, 2017

(54) SYSTEMS AND METHODS FOR HEART FAILURE MANAGEMENT

(71) Applicant: CARDIAC PACEMAKERS, INC., St. Paul, MN (US)

(72) Inventors: Ramesh Wariar, Blaine, MN (US); Pramodsingh Hirasingh Thakur, Woodbury, MN (US); Viktoria A. Averina, Roseville, MN (US); Yi Zhang, Plymouth, MN (US); Qi An, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 67 days.

(21) Appl. No.: 14/478,326

(22) Filed: Sep. 5, 2014

(65) Prior Publication Data
US 2015/0073203 A1 Mar. 12, 2015

Related U.S. Application Data

(60) Provisional application No. 61/874,693, filed on Sep. 6, 2013.

(51) Int. Cl.
*A61M 1/12* (2006.01)
*A61M 1/10* (2006.01)
(Continued)

(52) U.S. Cl.
CPC ......... *A61M 1/1086* (2013.01); *A61N 1/3702* (2013.01); *A61N 1/3962* (2013.01);
(Continued)

(58) Field of Classification Search
CPC .. A61N 1/3702; A61N 1/3627; A61N 1/3962; A61B 5/4836; A61B 5/024;
(Continued)

(56) References Cited

U.S. PATENT DOCUMENTS 6,076,015 A 6/2000 Hartley et al.
6,116,862 A 9/2000 Rau et al.
(Continued)

OTHER PUBLICATIONS

Bartoli, Carlo R. et al., "Increased Intrathoracic Impedance May Predict Adverse Events in LVAD Patients," J. Card Surg, XX:1-3, 2013, pp. 1-3.
(Continued)

*Primary Examiner* — Tammie K Heller
(74) *Attorney, Agent, or Firm* — Schwegman Lundberg & Woessner, P.A.

(57) ABSTRACT

The present document discusses medical device systems and related methods. In an embodiment, a medical device system can include a cardiac device. The cardiac device can include a processor, a memory, a communications circuit, and one or more sensors. The cardiac device can be configured to engage a sensor mode specific for patients receiving or having implanted ventricular assist devices. The cardiac device can be configured to process data as specified by the sensor mode specific for patients receiving or having implanted ventricular assist devices. In an embodiment, a method for monitoring heart failure patients is discussed. In an embodiment, a method of controlling devices for heart failure patients is discussed. Other embodiments are also included herein.

19 Claims, 9 Drawing Sheets

(51) Int. Cl.
*A61N 1/37* (2006.01)
*A61N 1/39* (2006.01)

(52) U.S. Cl.
CPC ..... *A61M 1/122* (2014.02); *A61M 2205/3303* (2013.01); *A61M 2205/3334* (2013.01); *A61M 2205/502* (2013.01); *A61M 2230/04* (2013.01)

(58) Field of Classification Search
CPC ................ A61M 1/1086; A61M 1/122; A61M 2230/04; A61M 2205/3303
See application file for complete search history.

(56) References Cited

U.S. PATENT DOCUMENTS

| | | |
|---|---|---|
| 6,237,398 B1 | 5/2001 | Porat et al. |
| 6,937,900 B1 | 8/2005 | Pianca et al. |
| 7,077,801 B2 | 7/2006 | Haverich et al. |
| 7,172,551 B2 | 2/2007 | Leasure et al. |
| 7,494,459 B2 | 2/2009 | Anstadt et al. |
| 8,187,199 B2 | 5/2012 | Patangay et al. |
| 8,216,834 B2 | 7/2012 | Colloca et al. |
| 8,277,389 B2 | 10/2012 | Carlson et al. |
| 8,364,263 B2 | 1/2013 | Patangay et al. |
| 8,774,919 B2 * | 7/2014 | Doerr .................. A61M 1/1086 607/16 |
| 2008/0243016 A1 | 10/2008 | Liao et al. |
| 2011/0178361 A1 * | 7/2011 | Yomtov .................. A61M 1/10 600/16 |
| 2011/0270331 A1 * | 11/2011 | Peters .................. A61M 1/1068 607/3 |
| 2012/0157856 A1 | 6/2012 | An et al. |

OTHER PUBLICATIONS

Slaughter, Mark S. et al., "Clinical Management of Continuous-Flow Left Ventricular Assist Devices in Advanced Heart Failure," The Journal of Heart and Lung Transplantation, vol. 29, No. 4S Apr. 2010, pp. S1-S39.

Stevenson, Lynne W. et al., "Intermacs Profiles of Advanced Hearth Failure: The Current Picture," The Journal of Heart and Lung Transplantation, vol. 28, No. 6, Jun. 2009, pp. 535-541.

* cited by examiner

SYSTEMS AND METHODS FOR HEART FAILURE MANAGEMENT

FIELD

The present disclosure relates to medical device systems and related methods. More specifically, the present disclosure relates to medical device systems for use with heart failure patients and related methods.

BACKGROUND

Ventricular assist devices (VAD) are used to provide care to advanced heart failure patients requiring mechanical circulatory support. VADs generally operate by taking blood from one point (such as the left ventricle) and delivering it to another point (such as the aorta) with sufficient force to assist the patient's heart in pumping blood. VADs can include continuous-flow and pulsatile-flow devices. More recently, continuous-flow devices have become the standard of care due to various aspects such as mechanical longevity and reliability. Amongst VADs, left ventricular assist devices (LVADs) are much more common than right ventricular assist devices (RVADs). However, both types are in use. VADs were originally only used as a bridge to transplant. However, more recently, some VADs have been approved as destination therapy.

SUMMARY

Embodiments include medical device systems and related methods. In an embodiment, the disclosure includes a medical device system. The medical device system can include a cardiac device. The cardiac device can include a processor, a memory, a communications circuit, and one or more sensors. The cardiac device can be configured to engage a sensor mode specific for patients receiving or having implanted VADs. The cardiac device can be configured to process data as specified by the sensor mode specific for patients receiving or having implanted VADs.

In an embodiment, the disclosure includes a method for monitoring heart failure patients. The method can include selecting patients receiving or having an implanted VAD and having a cardiac device. The method can further include sending instructions to the cardiac device to engage a sensor mode specific for patients receiving or having implanted VADs. The method can further include processing data on the cardiac device as specified by the sensor mode specific for patients having implanted VADs. In some embodiments, the method can include sending data from the cardiac device to the implanted VAD.

In an embodiment, the disclosure includes a method of controlling devices for heart failure patients. The method of controlling devices for heart failure patients can include selecting patients having an implanted VAD and having a cardiac device, sending instructions to the cardiac device to engage an operation mode specific for patients having implanted VADs, evaluating sensor data from the cardiac device, and generating directives regarding operational parameters of the implanted VAD.

In an embodiment, the disclosure includes a method of controlling devices for heart failure patients. The method of controlling devices for heart failure patients can include selecting patients having an implanted VAD and having an implanted cardiac rhythm management device, sending instructions to the implanted cardiac rhythm management device to engage an operation mode specific for patients having implanted VADs, evaluating sensor data from the implanted cardiac rhythm device, and adjusting operational parameters of the implanted cardiac rhythm management device based on the sensor data.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present disclosure is defined by the appended claims and their legal equivalents.

BRIEF DESCRIPTION OF THE FIGURES

The disclosure may be more completely understood in connection with the following drawings, in which.

While the disclosure is susceptible to various modifications and alternative forms, specifics thereof have been shown by way of example and drawings, and will be described in detail. It should be understood, however, that the disclosure is not limited to the particular embodiments described. On the contrary, the intention is to cover modifications, equivalents, and alternatives falling within the spirit and scope of the disclosure.

DETAILED DESCRIPTION

The embodiments of the present disclosure described herein are not intended to be exhaustive or to limit the disclosure to the precise forms disclosed in the following detailed description. Rather, the embodiments are chosen and described so that others skilled in the art can appreciate and understand the principles and practices of the present disclosure.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Figure 1:
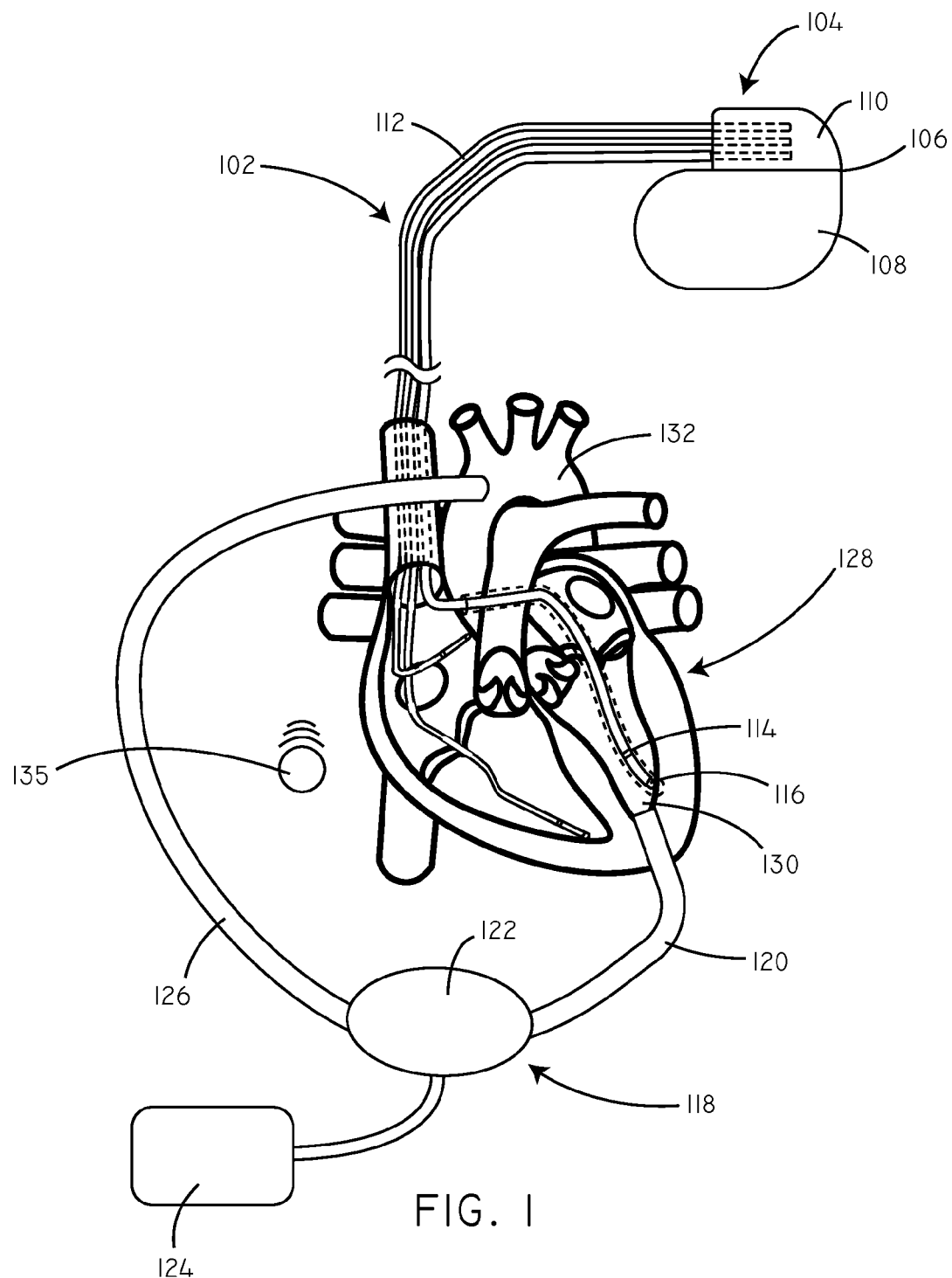
FIG. 1 is a schematic view of medical device system interfacing with a human heart in accordance with various embodiments herein.

Embodiments herein can include cardiac devices that can operate in conjunction with ventricular assist devices (VADs). Referring now to FIG. 1, the medical device system 102 includes a cardiac device 104. In some embodiments, the cardiac device 104 can be an implanted cardiac rhythm management (CRM) device 106. CRM devices can include, but are not limited to, pacemakers, implantable cardioverter defibrillators (ICDs), cardiac resynchronization therapy devices, cardiac monitors, neurostimulators, and the like.

The cardiac device 104 can include a pulse generator 108. The pulse generator 108 can serve to house various elements for operation of the device such as a controller, battery, memory, sensors, and the like. Further details regarding elements of exemplary devices are provided below. The cardiac device 104 can also include a header 110. The cardiac device 104 can include leads 112 that can be connected to the header 110. It will be appreciated the number of leads can range from one to eight or more. The leads 112 can include a ring electrode 114 and a tip electrode 116. Although some leads may only include a single electrode. Other leads may include more than two electrodes. Still other leads may not include electrodes but may include other functional elements such as sensors. In some embodiments, the pulse generator 108 housing can serve as an electrode. In some embodiments, a separate sensor 135 can also be included. The separate sensor 135 can be implanted or can be external. The separate sensor can communicate with other system components wirelessly or through wired connections.

The medical device system 102 can include a VAD 118. The VAD 118 can include an inflow cannula 120. The inflow cannula 120 can be positioned so that blood is withdrawn from the left ventricle 130 of the human heart 128. The VAD 118 can include a pumping unit 122. The VAD 118 can include a control unit 124. The VAD 118 can further include outflow cannula 126. The outflow cannula 126 can be positioned so that blood is returned to the aorta 132 (in the context of an LVAD). Exemplary VADs are described in U.S. Pat. Nos. 6,116,862 and 7,077,801, the content of which is herein incorporated by reference. Exemplary VADs can specifically include continuous-flow and pulsatile-flow devices. VADs can also specifically include left ventricular assist devices (LVADs), right ventricular assist devices (RVADs), or both.

Figure 2:
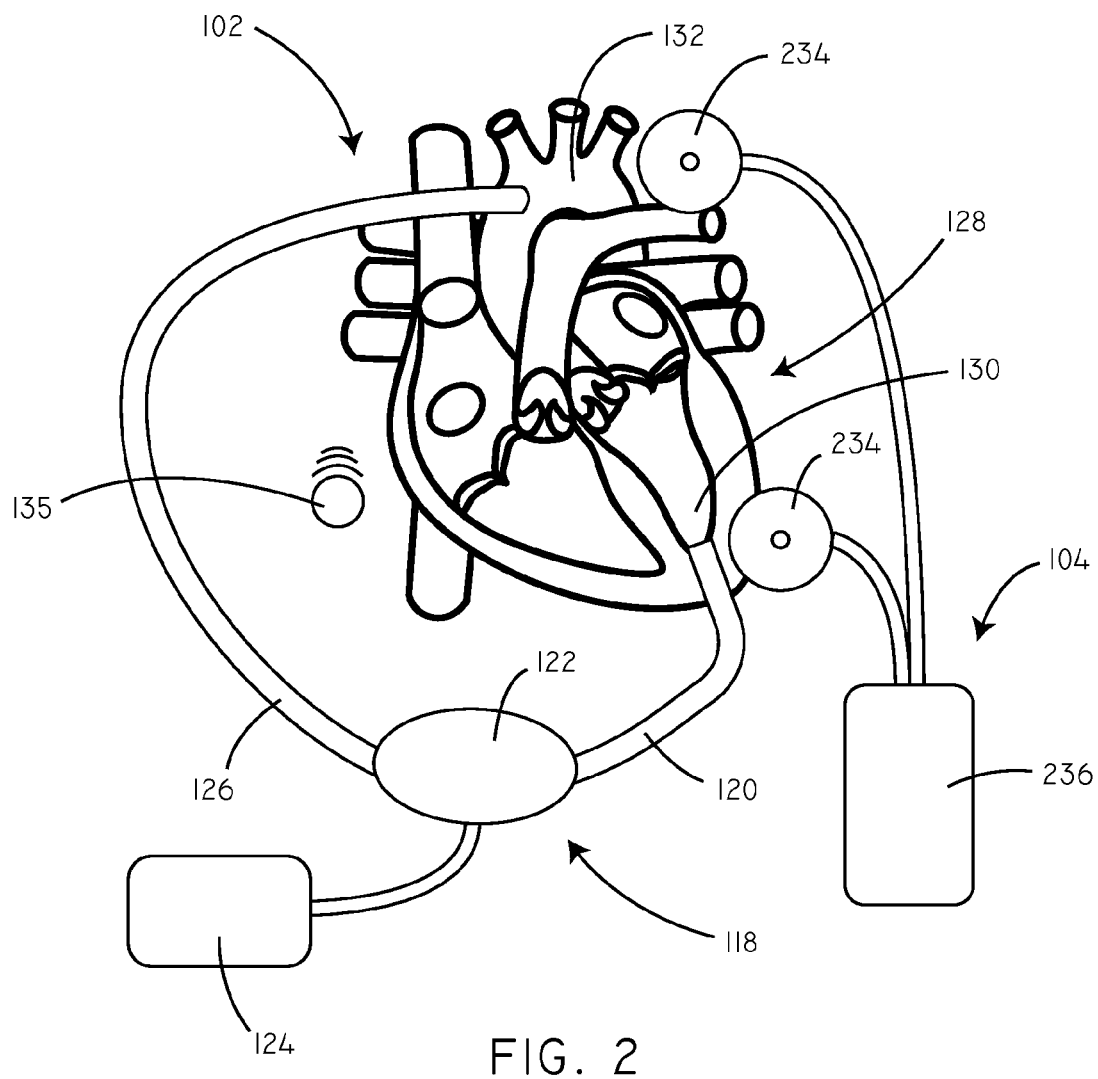
FIG. 2 is a schematic view of medical device system interfacing with a human heart in accordance with various embodiments herein.

It will be appreciated that cardiac devices in accordance with embodiments herein can be implanted or can be external. Referring now to FIG. 2, the medical device system 102 includes a cardiac device 104. In this embodiment, the cardiac device 104 includes an external monitor device 236. The cardiac device 104 also includes one or more sensors 234. The cardiac device 104 can also include a separate sensor 135 that can be implanted or external. The medical device system 102 can include a VAD 118. The VAD 118 can include an inflow cannula 120. The VAD 118 can include a pumping unit 122. The VAD 118 can further include a control unit 124. The VAD 118 can further include an outflow cannula 126. FIG. 2 also shows a human heart 128, including a left ventricle 130, and an aorta 132.

Sensors in accordance with embodiments herein can include both those that are implanted as well as those that are external. Sensors in accordance with embodiments herein can include, but are not limited to, an activity level sensor, a posture sensor, an accelerometer, a respiration sensor, a heart sounds sensor, an acoustic sensor, a blood pressure sensor, an impedance sensor (including transthoracic as well as intracardiac across multiple vectors), an optical sensor, a chemical sensor, or other sensors. Exemplary chemical sensors are described in U.S. Pat. No. 8,216,834, the content of which is herein incorporated by reference. Exemplary pressure sensors are described in U.S. Pat. No. 6,237,398, the content of which is herein incorporated by reference. Exemplary accelerometers are described in U.S. Pat. No. 6,937,900, the content of which is herein incorporated by reference.

Figure 3:
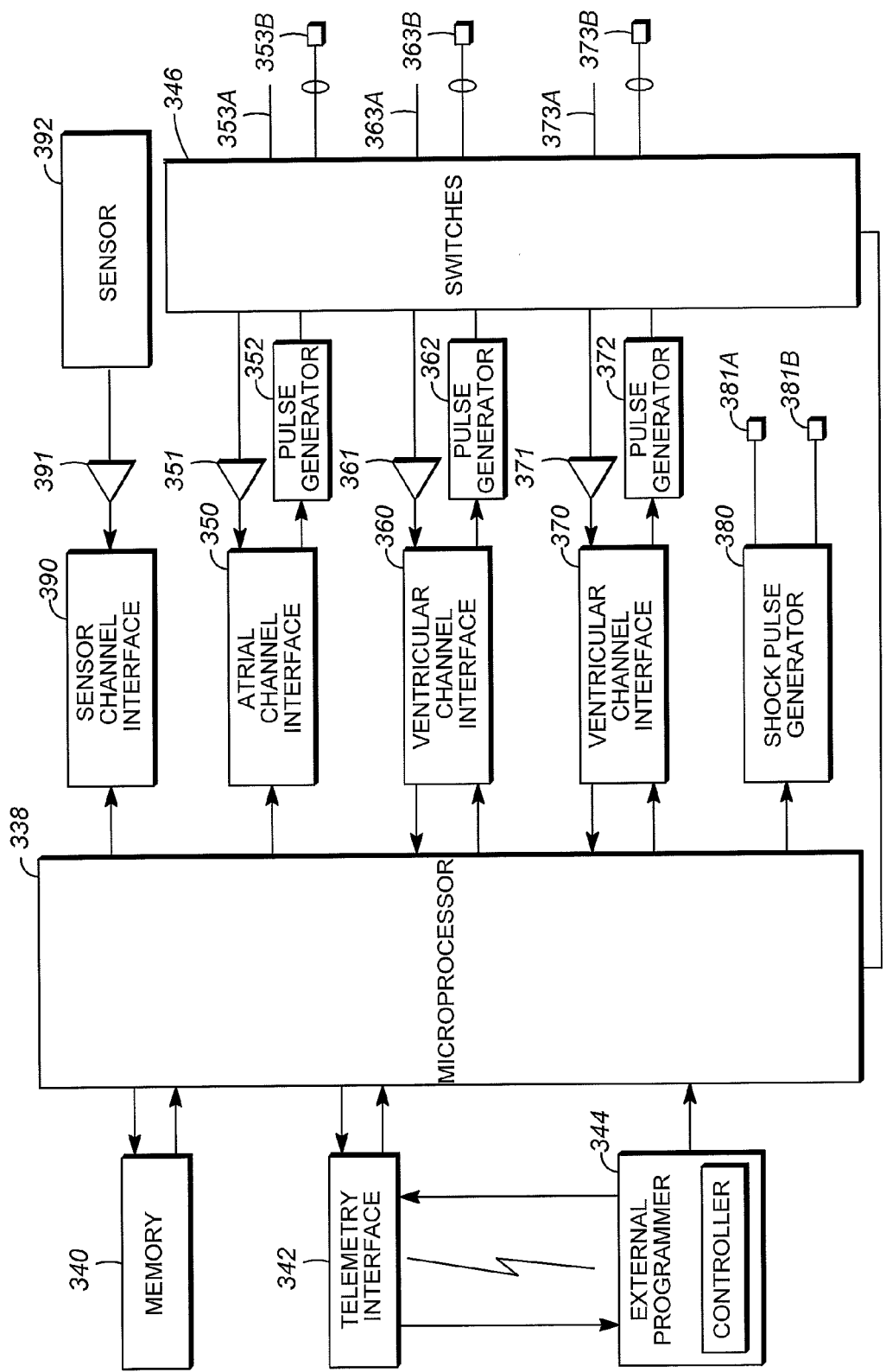
FIG. 3 is a schematic view of various elements of a cardiac device in accordance with various embodiments herein.

Referring now to FIG. 3, some components of an exemplary implantable cardiac rhythm management device 106 are schematically illustrated. The CRM device 106 can include a controller including a microprocessor 338 communicating with a memory 340, where the memory 340 may comprise a ROM (read-only memory) for program storage and a RAM (random-access memory) for data storage, and or other types of volatile or non-volatile memory. It will be appreciated that the controller could also be implemented by other types of logic circuitry (e.g., discrete components or programmable logic arrays) using a state machine type of design. The controller is capable of operating CRM device 106 in a number of programmed modes as well as being configured to execute various operations as described in greater detail below.

A communications circuit 342, such as a telemetry interface, is provided for communicating with an external programmer 344 or other device. The external programmer 344 can be a computerized device with a controller that can interrogate the CRM device 106 and receive stored data as well as adjust the operating parameters of the pacemaker.

The CRM device 106 has an atrial sensing/pacing channel comprising ring electrode 353A, tip electrode 353B, sense amplifier 351, pulse generator 352, and an atrial channel interface 350 which communicates bi-directionally with a port of microprocessor 338. In this embodiment, the device also has two ventricular sensing/pacing channels that similarly include ring electrodes 363A and 373A, tip electrodes 363B and 373B, sense amplifiers 361 and 371, pulse generators 362 and 372, and ventricular channel interfaces 360 and 370. For each channel, the electrodes are connected to the CRM device 106 by a lead or wirelessly and can be used for both sensing and pacing. A MOS (metal oxide semiconductor) switching network 346 (or similar switching device) can be controlled by the microprocessor and can be used to switch the electrodes from the input of a sense amplifier to the output of a pulse generator. A shock channel can also be provided comprising a shock pulse generator 380 and shock electrodes 381A and 381B that enable the device to deliver a defibrillation shock to the heart when fibrillation or other tachyarrhythmia is detected. The CRM device 106 can also include a sensing channel that comprises a sensor channel interface 390 and a sense amplifier 391 connected (wirelessly or through wired connections) to a sensor 392 (which can be implanted or external).

The channel interfaces can include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or adjusting the pacing pulse energy by changing the pulse amplitude or pulse width. The microprocessor 338 controls the overall operation of the device in accordance with programmed instructions stored in memory. The sensing circuitry of the CRM device 106 generates atrial and ventricular sense signals when voltages sensed by the electrodes exceed a specified threshold. The controller can then interpret sense signals from the sensing channels and control the delivery of paces in accordance with a programmed operations mode. The sensed signals from any of the sensing channels of the CRM device 106 in FIG. 3 can be digitized and recorded by the controller to constitute an electrogram that can either be transmitted via the telemetry interface 342 to the external programmer 344 or stored for later transmission. The patient's cardiac activity may thus be observed in real-time or over a selected historical period.

Figure 4:
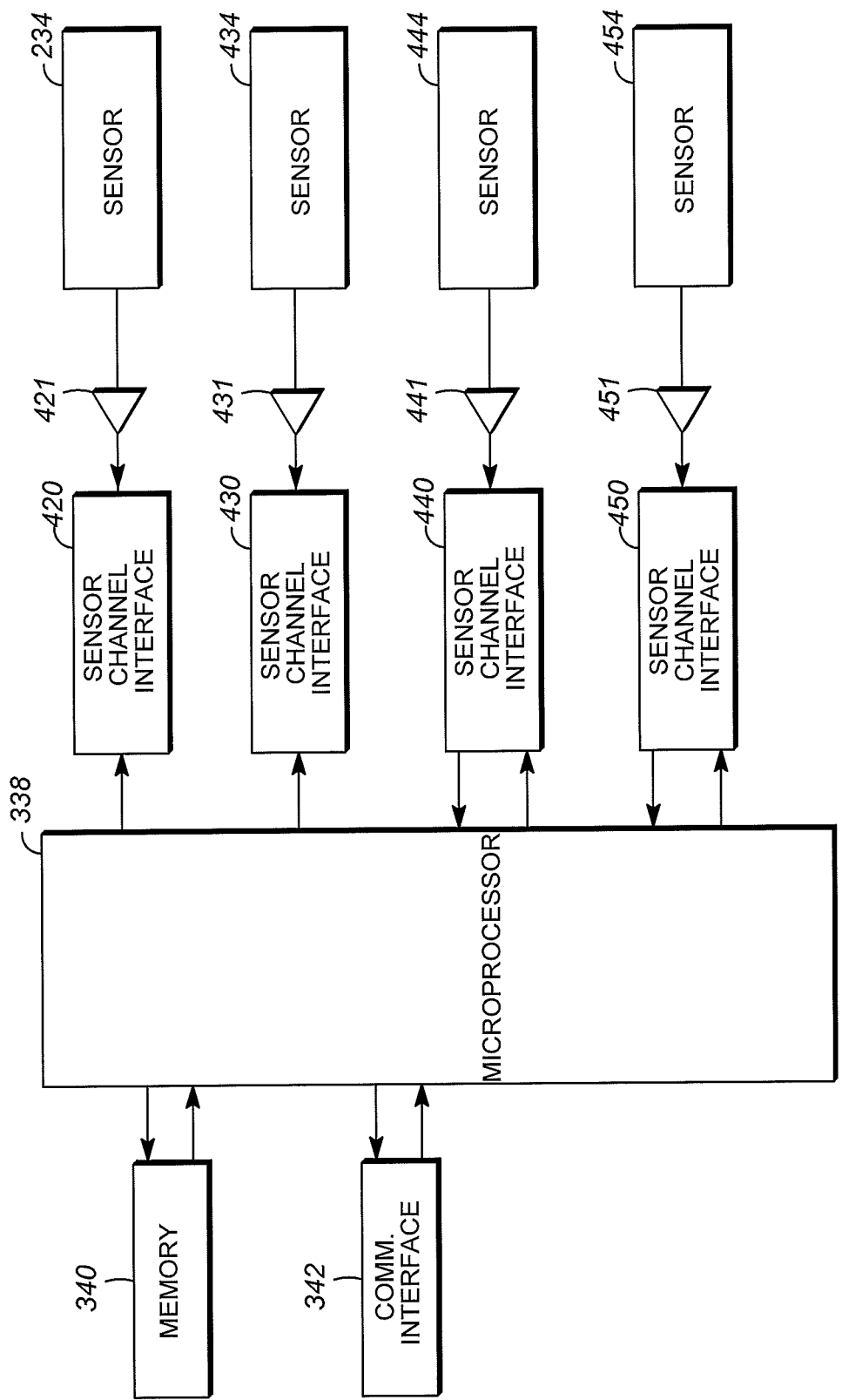
FIG. 4 is a schematic view of various elements of a cardiac device in accordance with various embodiments herein.

Referring now to FIG. 4, some components of an exemplary external monitor device 236 are schematically illustrated. The external monitor device 236 can include a controller made up of a microprocessor 338 communicating with a memory 340, where the memory 340 may comprise a ROM (read-only memory) for program storage and a RAM (random-access memory) for data storage, and or other types of volatile or non-volatile memory. It will be appreciated that the controller could be implemented by other types of logic circuitry (e.g., discrete components or programmable logic arrays) using a state machine type of design. The controller is capable of operating external monitor device 236 in a number of programmed modes as well as being configured to execute various operations as described in greater detail below.

A communications circuit 342, such as a communications interface, is provided for communicating with other external and internal devices. The external monitor device 236 can include one or multiple sensors and sensor channel interfaces. For example, in this embodiment, the external monitor device 236 can include sensing channels that include sensor channel interfaces 420, 430, 440, and 450, sense amplifiers 421, 431, 441, and 451, connected to sensors 234, 434, 444, and 454. The sensors themselves can be implanted or external and can communicate wirelessly or through wired connections.

The channel interfaces can include, but are not limited to, analog-to-digital converters for digitizing sensing signal inputs from the sensing amplifiers, registers that can be written to for adjusting the gain and threshold values of the sensing amplifiers. The microprocessor 338 controls the overall operation of the device in accordance with programmed instructions stored in memory. The signals from any of the sensing channels of the external monitor device 236 in FIG. 4 can be digitized and recorded by the controller. With regard to both FIGS. 3 and 4, it will be appreciated that these are provided only by way of illustration of some exemplary components of systems herein and it will be appreciated that in some embodiments less than all of the elements shown might be included while in other embodiments additional elements not show might be included.

Methods

Figure 5:
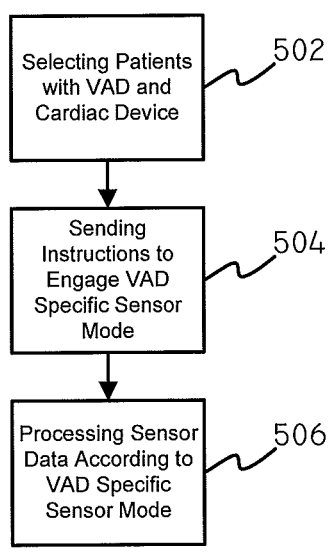
FIG. 5 is a flow chart of a method in accordance with various embodiments herein.

In an embodiment, the disclosure includes a method for monitoring heart failure patients with cardiac devices and VADs and adjusting operation of one or both devices to optimize the patient's hemodynamic and physiologic status. Referring now to FIG. 5, a flow chart of a method in accordance with various embodiments herein. In a first operation 502, the method can include selecting patients receiving or having an implanted ventricular assist device (VAD) and having a cardiac device (implanted or external). In some embodiments, patients can be selected based on information as provided by a care provider. In other embodiments, patients can be selected by the system through detection of characteristic properties of a patient with a VAD as measured by one or more sensors in the cardiac device such as changes in one or more of the amplitude, frequency, or morphology of pulse pressure variations in or around the heart. In an embodiment, the system can detect changes in one or more of the amplitude, frequency, or morphology of pulse pressure variations in or around the heart that are characteristic of a patient with a VAD.

In a second operation 504, the method can include sending instructions to the cardiac device to engage a sensor mode specific for patients receiving or having implanted VADs. As an example, sensor modes can be selected from the group consisting of a VAD patient candidacy mode (e.g., a mode to determine whether a given patient is an appropriate candidate for a VAD), a VAD intraoperative mode (e.g., a mode to be engaged while the patient is undergoing an operation to receive a VAD), a VAD post-operative mode, and a VAD ambulatory mode.

The VAD patient candidacy mode enables the clinician to screen-out patients who may not be indicated for VAD insertion, and in the remaining patients, optimize clinical status prior to implant. The VAD intraoperative mode is used to collect and transmit/display sensor data during the LVAD implant procedure. The VAD post-op mode optimizes patient status and minimizes device adverse effects while the patient recovers from the implant. The VAD ambulatory mode is used to ensure that patient status remains stable after the patient has recovered from the VAD implant (and could be a permanent mode of operation in patients who are stable after VAD implants).

In a third operation 506, the method can include processing data on the cardiac device as specified by the sensor mode specific for patients having implanted VADs. These modes can include one or more of emphasizing specific sensors or patient parameters that are detected by the cardiac device, changing sensor sampling frequencies, changing data smoothing parameters, changing baseline windows, changing algorithms used for discriminating abnormal from normal ranges, and alert thresholds. For example in the VAD patient-candidacy mode the CRM device can increase sensor detection of specific conditions that may complicate LVAD implant such as RV dysfunction, COPD exacerbation, etc. Sensor measurements can be generated at very high rates (e.g. once every 1 to 10 s) in the VAD intra-op mode to moderate rates (e.g. once every 10 s to 5 min; or slower than the intra-op rate) in the VAD post-op mode to still slower rates (e.g. 5 min to 4 hrs; or slower than the intra-op rate and/or VAD post-op mode) in the VAD ambulatory mode or VAD patient candidacy mode.

In accordance with the sensor mode specific for patients having implanted VADs, the cardiac device can be configured to detect changes in cardiac morphology and function for example, the degree of septal shift. There are various ways in which septal shift can be calculated. In some embodiments, the cardiac device can be configured to calculate a degree of septal shift using an intracardiac impedance signal. By way of example, decreases in the intracardiac impedance signal measured between one or more electrodes on the RA lead to the RV tip or ring electrode versus a baseline value can be an indication of septal shift. Also, by way of example, decreases in the intracardiac impedance signal measured between two electrodes on the RV tip versus a baseline value can be an indication of septal shift. In some embodiments, evaluating different specific intracardiac impedance measures as taken along different impedance vectors in comparison to baseline values and/or in comparison to impedance values across other specific vectors can be indicative of septal shift. As a further example, an increased leftward shift of the septum can result in a decrease in RA to RV impedance and an increase in RV to LV impedance.

In accordance with the sensor mode specific for patients having implanted VADs, the cardiac device can be configured to evaluate native LV pump function. LVAD flow when set to optimal values can increase native LV pump function by unloading the LV and increasing contractility. In contrast when LVAD flow is set too high, it increases LV suction which must be overcome by the native LV to eject blood through the aortic valve. In high LVAD flow conditions the LV cannot generate sufficient pressure to eject blood and a pulse is minimal or absent. Pulsatility is important to prevent vascular stiffening and to maintain myocardial perfusion. Therefore maintaining native LV pump function and pulsatility may be advantageous. LVAD function and its effect on native LV pump function can be determined both acutely and chronically using a number of cardiac device sensors.

Calculating or estimating LV pump function can include evaluating heart sounds features including one or more of amplitude, energy, frequency, morphology, etc. By way example, heart sounds can be evaluated against a baseline value and/or the magnitude of specific heart sounds can be evaluated against its baseline value or the magnitude of other heart sounds in order to calculate or estimate LV pump function. If LV pump flow is optimal, the improvement in LV contractility can be detected from the Si heart sound (associated with mitral valve closure at the start of contraction) Aspects of assessing contractility using the S1 heart sound are described in U.S. Pat. Nos. 8,187,199 and 8,277,389, the content of which is herein incorporated by reference. Improvements in LV contractility can also be detected using systolic timing intervals such as pre-ejection period and ejection time. Aspects of systolic interval analysis are described in U.S. Pat. No. 8,364,263 (Patangay et al.), the content of which is herein incorporated by reference Improvements in LV filling can also be detected using diastolic timing intervals such as S2-to-S1 interval or S2-to-Q wave marker. Inability of the native LV to eject its blood volume may also be detected from the S2 heart sound (associated with aortic valve closing). An absence or decrease in S2 and its associated intervals when compared with a baseline value can be indicative of an incomplete ejection. Changes in mitral or aortic valve insufficiency can be detected via heart sound murmurs.

In accordance with the sensor mode specific for patients having implanted VADs, the cardiac device can be configured to evaluate an intracardiac impedance vector. In some embodiments, evaluating different specific intracardiac impedance measures as taken along different vectors in comparison to baseline values and/or in comparison to impedance values across other specific vectors can be indicative of the status of the patient. Measurements of intracardiac impedance can be used to determine stroke volume of the native LV and in combination with S2 heart sound can be used to determine if ejection was successful. Native LV function can be chronically measured and trended in an LVAD patient. These trends can be used to control LVAD function either manually, or using a clinician assisted control system, or using a completely automatic closed-loop system to optimize native LV function.

In accordance with the sensor mode specific for patients having implanted VADs, the cardiac device can be configured to estimate volume status. Volume status relates to fluid build-up in the body and particularly in the thoracic region of a patient. Estimating volume status can include evaluating heart sounds (including, but not limited to, the third heart sound), intrathoracic impedance, pulmonary artery pressure, left atrial pressure (direct or estimated from pulmonary artery pressure), right atrial pressure, and/or systemic venous pressure. Aspects of evaluating volume status of a patient as well as heart sounds are described in U.S. Publ. Pat. Appl. No. 2012/0157856, the content of which is herein incorporated by reference.

In accordance with the sensor mode specific for patients having implanted VADs, the cardiac device can be configured to estimate a pressure in the left ventricle, right ventricle, and systemic arterial pressure. The method for monitoring heart failure patients can include an estimating a pressure at the inflow or outflow of the VAD using data from the VAD and receiving that data regarding pressure with the cardiac rhythm device.

The method for monitoring heart failure patients can include estimating a systolic pressure. The method for monitoring heart failure patients can also include estimating a diastolic pressure.

The method for monitoring heart failure patients can also include functions of the above measurements such as average systemic blood pressure (avBP), native LV pump function (LVnf), and volume status (VS). For example, the system can calculate:

$$LVADI = avBP \times LVnf / VolStatus.$$

As described above native LV function may be determined from functions S1, S2, STIs, intracardiac impedance, systolic pressure, diastolic pressure, and pulse pressure. Volume status (wherein higher numbers implying increased volume retention/redistribution) can be determined using right or left sided filling pressures and/or pulmonary impedance.

In accordance with the sensor mode specific for patients having implanted VADs, the cardiac device can be configured to estimate hemolysis. Hemolysis can be detected using a number of sensors such as impedance, or optical (transmittance/reflectance). Impedance measured in the blood pool from a pacemaker lead can be used to detect hemolysis. Similarly optical attenuation measurements in the heart via lead based sensors, or from tissue (muscle) using a sensor integrated in the PG or a subcutaneous or external device can be used to detect hemolysis.

In accordance with the sensor mode specific for patients having implanted VADs, the cardiac device can be configured to calculate at least one of respiration rate, tidal volume, rapid shallow breathing index, minute ventilation and heart rate. It will be appreciated that there are various ways of calculating these parameters, including but not limited to using impedance data and/or accelerometer data. Exemplary techniques are described in U.S. Publ. Appl. No. 2008/0243016; U.S. Pat. No. 6,076,015; and U.S. Publ. Pat. Appl. No. 2012/0157856, the content of all of which is herein incorporated by reference.

In accordance with the sensor mode specific for patients having implanted VADs, the cardiac device can be configured to estimate the patient's physiological response to activity and/or effort. Estimating the patient's physiological response to activity can include calculating at least one of heart rate, arrhythmia burden, heart sounds (especially the S1 heart sound as a surrogate for contractility), blood pressure, minute ventilation, respiration rate, tidal volume and rapid shallow breathing index at one or more activity levels.

The relationship of S1 with patient activity can be measured by detecting transitions of the patient from increased activity to rest (i.e. low activity) and measuring S1 immediately following the onset of a rest period. Since S1 measurement typically requires a constant heart rate and the patient's HR will decline to resting levels, the pacemaker can be configured to keep HR elevated for the duration of heart sound measurement. For example the pacemaker can be configured to keep the HR elevated for a period of about 30 s or more. Data collected at similar activity levels can then be averaged and trended over time.

In accordance with the sensor mode specific for patients having implanted VADs, the cardiac device can be configured to calculate a measure of variation of cardiac cycle intervals, a measure of variation of respiratory cycle intervals, tracking patient weight, and calculating arrhythmia burden.

In some embodiments, the ventricular device can be equipped with electrodes in order to measure impedance, including but not limited to, electrodes on opposites sides of a cannula (inflow or outflow). In some embodiments, the cardiac device can be configured to receive cross-cannular impedance data from an implanted VAD. In some embodiments, the cardiac device can be configured to calculate blood flow velocity using cross-cannular impedance data from an implanted VAD.

In some embodiments, the cardiac device can be configured to calculate or estimate right ventricle (RV) function. In some embodiments, the cardiac device can be configured to calculate a RV volume trend. In some embodiments, the cardiac device can be configured to calculate or estimate RV volume by evaluating intracardiac impedance signals (including absolute values, comparative values, changes in values, and/or trends in values). However, it will be appreciated that there are other ways of calculating or estimating RV volume.

Figure 6:
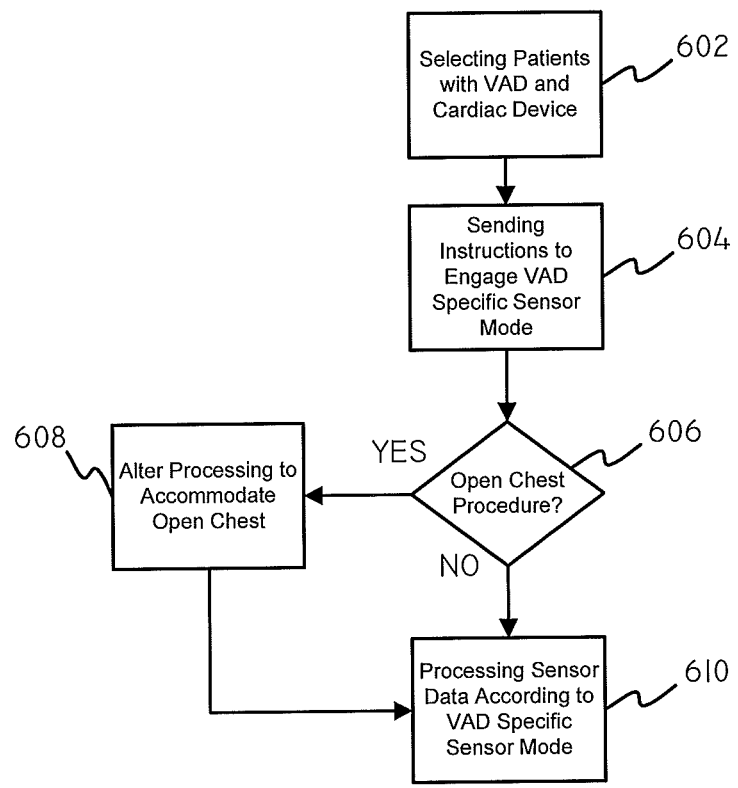
FIG. 6 is a flow chart of a method in accordance with various embodiments herein.

Referring now to FIG. 6, a flow chart of a method in accordance with various embodiments herein. In a first operation 602, the method can include selecting patients receiving or implanted with a ventricular assist device (VAD) and a cardiac device (implanted or external). In a second operation 604, the method can include sending instructions to a cardiac device to engage a VAD specific sensor mode. The cardiac device can be configured to receive instructions including an indication of whether the patient is undergoing a surgical procedure in the thoracic cavity of the patient such as an open chest procedure.

In a third operation 606, the method can include evaluating whether the patient is undergoing an open chest procedure. If so, then in a fourth operation 608, the method can include altering processing of sensor data if an indication of an open chest procedure is received.

Altering processing of sensor data based on an indication of an open chest procedure can be effective to mitigate an adverse impact on sensor data collection. In some embodiments, altering processing includes an opportunistic change in the way data is collected to optimize gathering of pertinent information for a current patient condition. In some embodiments, altering processing includes adjusting the baseline for one or more sensors being used. For example, altering processing can include adjusting the baseline for one or more impedance sensors. In some embodiments, altering processing includes prioritizing the physiological signals based on their sensitivity to open chest procedure. In some embodiments, altering processing can include includes resetting data by discarding pre-procedure data. In some embodiments, altering processing includes changing sampling parameters of the sensor data.

In a fifth operation 610, the method can include processing sensor data according to the VAD specific sensor mode.

Figure 7:
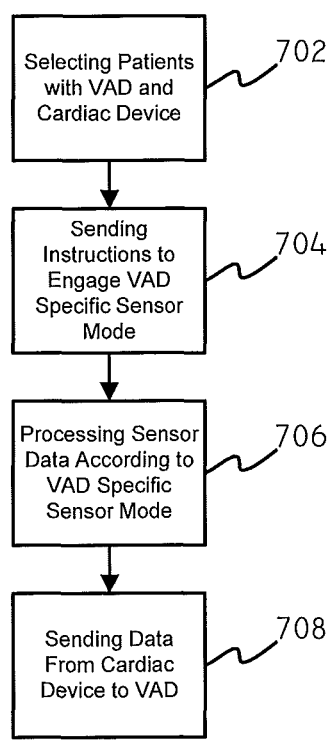
FIG. 7 is a flow chart of a method in accordance with various embodiments herein.

Referring now to FIG. 7, a flow chart of a method in accordance with various embodiments herein. In a first operation 702, the method can include selecting patients with a ventricular assist device (VAD) and a cardiac device (implanted or external). In a second operation 704, the method can include sending instructions to a cardiac device to engage a VAD specific sensor mode. In a third operation 706, the method can include processing sensor data according to the VAD specific sensor mode. In a fourth operation 708, the method can include sending data from the cardiac device to the VAD.

Figure 8:
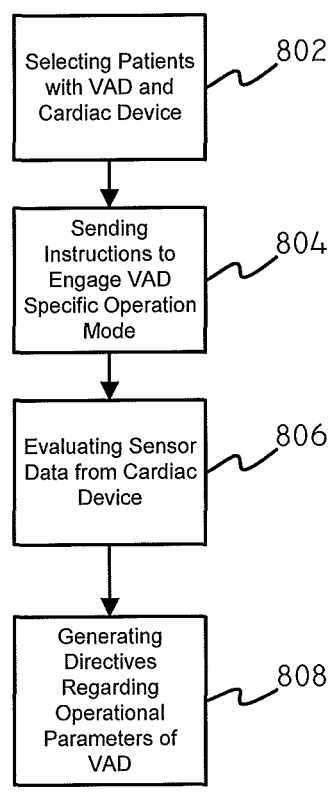
FIG. 8 is a flow chart of a method in accordance with various embodiments herein.

In an embodiment, the disclosure includes a method of controlling devices for heart failure patients. Referring now to FIG. 8, a flow chart of a method in accordance with various embodiments herein. In a first operation 802, the method can include selecting patients with a ventricular assist device (VAD) and a cardiac device (implanted or external). In a second operation 804, the method can include sending instructions to a cardiac device to engage a VAD specific sensor mode. In a third operation 806, the method can include evaluating sensor data from the cardiac device.

It will be appreciated that various types of sensor data can be evaluated in order to reach different types of conclusions regarding the condition of the patient. By way of example, in some embodiments various pieces of sensor data can be evaluated in order to determine the patient's activity or effort status. Such pieces of sensor data can include, but are not limited to, accelerometer sensor data, minute ventilation data (based on intrathoracic impedance sensor, or another type of sensor), and the like.

In some embodiments, various pieces of sensor data can be evaluated in order to determine the patient's volume status. Such pieces of data can include intrathoracic impedance, heart sounds, LAP (left atrial pressure), RAP (right atrial pressure), PAP (pulmonary artery pressure), central venous pressure, and intraabdominal pressure.

In a fourth operation 808, the method can include generating directives regarding operational parameters of a VAD. In some embodiments, this operation can be performed by the cardiac device. In other embodiments, this operation can be performed by an external programmer device.

In some embodiments, the directives can include recommendations provided to a system user regarding settings for operational parameters of the implanted VAD. In other embodiments, the directives can include instructions for closed loop control of the implanted VADs.

In some embodiments, the directive can regard the pump flow (for example, the pump flow rate) of the VAD. In continuous flow devices pump flow can be adjusted by changing the pump speed or rpm. Controlling can include increasing, decreasing, or maintaining the status quo of the current pump flow. In some embodiments, the directive can regard changing the pump flow of the VAD when the cardiac device detects a change in patient's posture. By way of example, an instruction or suggestion to decrease the pump flow of the VAD can be provided when the patient goes from an upright position to a recumbent position. As another example, an instruction to increase the pump flow of the VAD can be provided when the patient goes from a recumbent position to an upright position. As yet another example, an instruction to change the pump flow of the VAD can be provided when the cardiac device detects a change in the patient's effort. In some embodiments, detecting a change in a patient's effort is performed via analyzing data from at least one of an accelerometer sensor or a minute ventilation sensor. As another example, an instruction to change the pump flow of the VAD can be provided when the cardiac device detects a change in the patient's volume status. In some embodiments, detecting a change in the patient's volume status is evaluated through analysis of intrathoracic impedance, heart sounds, LAP (left atrial pressure), and PAP (pulmonary artery pressure). As another example, an instruction to change the pump flow of the VAD can be provided when the cardiac device detects a change in the patient's LV function or septal shift. In some embodiments, LV function is evaluated through analyzing heart sounds. In some embodiments the heart sound includes the S2 heart sound amplitude. In some embodiments, the method can further include separating out the pulmonic and aortic components of the S2 heart sound. In some embodiments the heart sound includes the S1 heart sound amplitude. In some embodiments, the method can further include separating out the mitral and tricuspid components of the S1 heart sound. In some embodiments, the method can further include measuring heart murmurs. In some embodiments, ventricular suction is evaluated through analysis of a trans-chamber impedance vector (LV-RV).

In some embodiments, the method includes controlling the speed of a RVAD, wherein controlling includes setting the speed to target speed that is the sum of a baseline speed and an adjustment speed; setting the baseline speed to be equivalent to the speed of the LVAD; and setting the adjustment speed; wherein the adjustment speed is increased if central congestion is too low and decreased if central congestion is too high. The adjustment speed can be set using specific profiles such as a ramp profile. In response to changes in the pump speed of the LVAD/RVAD, changes in sensor readings measured by the cardiac device such as ITTI, heart sounds, heart rate, respiration, etc. can be used to set the final pump speed.

In some embodiments, the method can further include estimating central congestion using intrathoracic impedance, S3 heart sound, LA Pressure, and LVEDP. In some embodiments, LVEDP is measured by the LVAD and can then be sent to the cardiac device.

Figure 9:
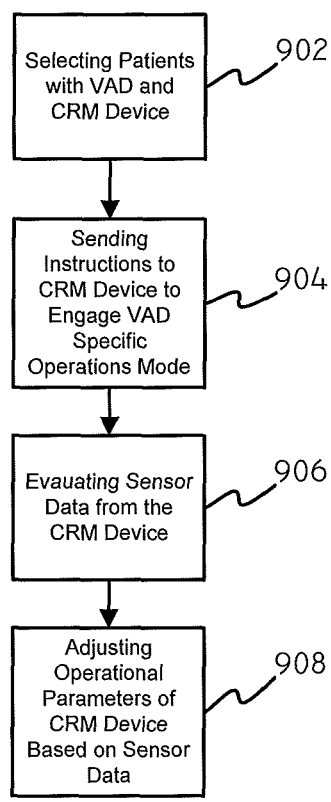
FIG. 9 is a flow chart of a method in accordance with various embodiments herein.

Referring now to FIG. 9, a flow chart of a method in accordance with various embodiments herein. In a first operation 902, the method can include selecting patients with a ventricular assist device (VAD) and a cardiac device (implanted or external) such as a CRM (cardiac rhythm management) device. In a second operation 904, the method can include sending instructions to a cardiac device to engage a VAD specific sensor mode. In a third operation 906, the method can include evaluating sensor data from the CRM device. In a fourth operation 908, the method can include adjusting operational parameters of the CRM device based on sensor data.

It will be appreciated that various operational parameters of the cardiac device can be adjusted. For example, in some embodiments for devices including pacemaker (pacing) functionality the parameters can include at least one parameter selected from the group consisting of atrioventricular delay, interventricular delay, lower rate limit, pacing voltage, pacing duration, pacing waveform, pacing vector, and pacing mode. Alternatively, in some embodiments, such as for neuromodulation devices, the parameters can include stimulation intensity, frequency, duty cycle, and profile. Alternatively, in some embodiments the parameters can include drug type, drug flow rate, and drug infusion profile.

It should be noted that, as used in this specification and the appended claims, the singular forms 'a,' 'an,' and 'the' include plural referents unless the content clearly dictates otherwise. Thus, for example, reference to a composition containing 'a compound' includes a mixture of two or more compounds. It should also be noted that the term 'or' is generally employed in its sense including 'and/or' unless the content clearly dictates otherwise.

It should also be noted that, as used in this specification and the appended claims, the phrase 'configured' describes a system, apparatus, or other structure that is constructed or configured to perform a particular task or adopt a particular configuration to. The phrase 'configured' can be used interchangeably with other similar phrases such as arranged and configured, constructed and arranged, constructed, manufactured and arranged, and the like.

All publications and patent applications in this specification are indicative of the level of ordinary skill in the art to which this disclosure pertains. All publications and patent applications are herein incorporated by reference to the same extent as if each individual publication or patent application was specifically and individually indicated by reference.

The disclosure has been described with reference to various specific and preferred embodiments and techniques. However, it should be understood that many variations and modifications may be made while remaining within the spirit and scope of the disclosure.

The invention claimed is:

1. A medical device system comprising:
  a cardiac device comprising;
    a controller;
    a memory;
    a communications circuit; and
    one or more sensors;
  wherein the cardiac device configured to:
    engage a sensor mode specific for patients receiving or having implantable ventricular assist devices different than and separate from the cardiac device;
    process data as specified by the sensor mode specific for the patients receiving or having the implantable ventricular assist devices; and
    generate or adjust operation parameters of the cardiac device or the implantable ventricular assist devices based on the processed data.

2. The medical device system of claim 1, the cardiac device comprising an implantable or external-cardiac rhythm management device.

3. The medical device system of claim 1, wherein the sensor mode specific for patients receiving or having implantable ventricular assist devices is selected from the group consisting of an candidacy mode, intraoperative mode, a post-operative hospital mode, and a post-operative ambulatory mode.

4. The medical device system of claim 1, wherein the cardiac device is configured to receive, via the communication circuit, instructions including an indication of whether the patient is undergoing an open chest procedure.

5. The medical device system of claim 4, wherein the cardiac device is configured to alter processing of sensor data if an indication of an open chest procedure is received.

6. The medical device system of claim 5, wherein altering processing includes evaluating the baseline for the sensors.

7. The medical device system of claim 5, wherein altering processing includes resetting data analysis by discarding pre-procedure data.

8. The medical device system of claim 5, wherein altering processing includes changing the rate at which sensor measurements are generated and/or displayed.

9. The medical device system of claim 1, wherein the cardiac device includes an impedance sensing circuit to calculate a degree of septal shift using an intracardiac impedance signal.

10. The medical device system of claim 1, wherein the cardiac device is configured to receive cross-cannular impedance data from an implantable ventricular assist device.

11. The medical device system of claim 10, wherein the cardiac device is configured to measure the cross-cannular impedance data from the implantable ventricular assist device.

12. The medical device system of claim 1, wherein the cardiac device is configured to calculate or estimate RV function.

13. The medical device system of claim 1, wherein the cardiac device is configured to calculate or estimate RV volume by evaluating intracardiac impedance signals.

14. The medical device of claim 1, wherein the cardiac device is configured to deliver a therapy according to the processed data.

15. The medical device of claim 14, wherein the therapy includes a cardiac therapy or a neurostimulation therapy.

16. A method for operating a medical device system to monitor heart failure patients receiving or having an implantable ventricular assist device and having a cardiac device different than and separate from the implantable ventricular assist device, the method comprising:

sending, via the medical device system, instructions to the cardiac device to engage a sensor mode specific for patients receiving or having implantable ventricular assist devices;

processing data, via the medical device system, on the cardiac device as specified by the sensor mode specific for patients having implantable ventricular assist devices; and generating or adjusting operation parameters of the cardiac device or the implantable ventricular assist devices based on the processed data.

17. The method of claim 16, wherein the sensor mode specific for patients receiving or having implantable ventricular assist devices is selected from the group consisting of an candidacy mode, intraoperative mode, a post-operative hospital mode, and a post-operative ambulatory mode.

18. The method of claim 16, wherein the instructions sent to the cardiac device includes an indication of whether the patient is undergoing an open chest procedure;

the method further comprising altering processing of sensor data if the indication of the open chest procedure is affirmative.

19. The method of claim 18, wherein altering the processing of sensor data includes evaluating the baseline for the sensors.

* * * * *